(12) United States Patent
Hood

(10) Patent No.: US 9,408,883 B2
(45) Date of Patent: Aug. 9, 2016

(54) **ESSENTIAL OIL OF *KUNZEA AMBIGUA* AND METHODS OF USE**

(71) Applicant: John James David Hood, Bridport (AU)

(72) Inventor: John James David Hood, Bridport (AU)

(*) Notice: Subject to any disclaimer, the term of this patent is extended or adjusted under 35 U.S.C. 154(b) by 0 days.

(21) Appl. No.: 13/969,623

(22) Filed: Aug. 19, 2013

(65) Prior Publication Data

US 2015/0050362 A1 Feb. 19, 2015

Related U.S. Application Data

(63) Continuation-in-part of application No. 13/090,640, filed on Apr. 20, 2011, now abandoned, which is a continuation-in-part of application No. 12/597,372, filed as application No. PCT/AU2008/000560 on Apr. 22, 2008, now abandoned.

(30) Foreign Application Priority Data

Apr. 23, 2007 (AU) ................................ 2007902118

(51) Int. Cl.
*A61K 36/185* (2006.01)
*A61K 36/61* (2006.01)
*A61K 31/015* (2006.01)

(52) U.S. Cl.
CPC ............... *A61K 36/61* (2013.01); *A61K 31/015* (2013.01)

(58) Field of Classification Search
None
See application file for complete search history.

(56) References Cited

PUBLICATIONS

Kappagoda (Mayo Clin. Proc. (2011), vol. 86, No. 6, pp. 561-583).*
Bloor, S. J., "Antiviral Phlorglucinols from New Zealand Kunzea Species," Journal of Natural Products, American Chemical Society, vol. 55, No. 1, pp. 43-47 (Jan. 1, 1992).
Lis-Blachin, M. et al., "Bioactivity of New Zealand Medicinal Plant Essential Oils," Acta Horticulture, Int'l Soc. for Horticulture Science, BE, No. 426, pp. 13-30 (Jan. 1996).
Lis-Blachin, M. et al, "Pharmacologial and antimicrobal studies on different tea-tree oils," Medicinal Aromatic Plaints Abstracts, vol. 23, No. 1, pp. 623-633 (Apr. 2001).
Khambay B. P. S. et al., "An insecticidal mixture from tetramethylcyclo-hexenedione isomers from Kunzea ambigua," Phytochemistry, vol. 59, No. 1, pp. 69-71 (Jan. 1, 2002).
Ito H. et al., "Kunzeanones A, B, and C: novel alkylated phloroglucinol metabolites from Kunzea ambigua," Tetrahedron, vol. 60, No. 44, pp. 9971-9976 (Oct. 25, 2004).
Veech, T., "Newsletter August 05," Internet Citation: http://www.NaturalSolutionsbyTia.com (Published: Aug. 2005).

* cited by examiner

*Primary Examiner* — Chris R Tate
*Assistant Examiner* — Randall Winston
(74) *Attorney, Agent, or Firm* — Edwin D. Schindler

(57) ABSTRACT

A method for treating disease includes the steps of obtaining the essential oil from the *Kunzea ambigua* plant and administering the essential oil obtained to a human to take internally. The essential oil of the *Kunzea ambigua* plant has been discovered to act positively against parasitic infestation of humans and animals, and also has been found to have high kill rates against various viral and bacterial infections.

8 Claims, No Drawings

ESSENTIAL OIL OF KUNZEA AMBIGUA AND METHODS OF USE

CROSS-REFERENCE TO RELATED PATENT APPLICATIONS

This is continuation-in-part of application Ser. No. 13/090,640, filed Apr. 20, 2011, now abandoned, which is a continuation-in-part application of Ser. No. 12/597,372, filed Oct. 23, 2009, which represents the U.S. National Phase application of P.C.T. Application No. PCT/AU2008/000560, filed Apr. 22, 2008, the entire disclosure of which shall be deemed incorporated by reference herein.

BACKGROUND OF THE INVENTION

1. Technical Field of the Invention

The present invention relates to the use of an essential oil of Kunzea ambigua and methods for its medicinal use in aiding in the treatment, or at least partially alleviating the effects, of various ailments, including certain parasitic infestations in humans and animals, such as those parasitic infestations that adversely affect digestion, irritable bowel syndrome, hemorrhoids, symptoms of the common cold, as well as improving the condition for lesions and ulcers of the type often attendant certain cancers, such as cancer of the jaw and mouth. Beneficial effects have also been observed with respect to scrub typhus (tick fever), certain sinus infections, whooping cough, tooth abscess and inflammation, including the inflammatory effects associated with auto-immune diseases, particularly, Crohn's disease.

2. Description of the Prior Art

The prior art known to the inventor includes the Kunzea ambigua websites (http://web.archive.org/web/20070405000622; http://www.aquasapone.com/kunzea.html) (Apr. 5, 2007), which explains that Kunzea ambigua has been found effective against several bacteria, including Staphylococcus aureas, E. coli and Candida albicans, in addition to helping to improve certain severe skin conditions, such as eczema, dermatitis, ulcers and chillblains.

Australia Patent No. 721,156 B2, entitled "Essential Oil and Methods of Use," describes the use of the essential oils from Kunzea ambigua for external applications for the treatment of medical conditions.

The totality of the prior art neither teaches nor suggests the use of Kunzea ambigua, nor a related method, for the treatment of digestive ailments and inflammatory conditions, among other beneficial uses, as taught herein.

SUMMARY OF THE INVENTION

It is therefore an object of the present invention to use the essential oil of Kunzea ambigua for the treatment of various digestive ailments, inflammatory conditions, tick fever, sinus infections, in addition to other beneficial uses.

The foregoing and related objects are accomplished by the present invention, which provides a method for treating such ailments as, or otherwise reducing the effects of, irritable bowel syndrome, hemorrhoids, symptoms of the common cold, improving the condition of lesions and ulcers of the type often attendant certain cancers, such as cancer of the jaw and mouth scrub typhus (tick fever), certain sinus infections, whooping cough, tooth abscesses and inflammation, including the inflammatory effects associated with auto-immune diseases, particularly, Crohn's disease, which method includes the steps of obtaining an essential oil of Kunzea ambigua and internally administering the essential oil of Kunzea ambigua via inhalation, ingestion or via application to an infected area, if feasible. For hemorrhoids, a suppository is preferred for administering treatment.

A particularly effective method for treating, or reducing the adverse effects of, various ailments wherein ingestion or application to an infected area of Kunzea ambigua would be beneficial is the ingestion or application (e.g., treatment of a tooth abcess) is take approximately three drops of the essential oil of Kunzea ambigua per 10 kilograms of body weight of the patient and to repeat the treatment with Kunzea ambigua every six hours for a minimum of at least two days and until significant improvement is observed, often in less than seven days. Other dosages, depending upon the ailment, might also be effective.

Other objects and features of the present invention will become apparent when considered in combination with the detailed description of certain preferred embodiments of the present invention. It should, however, be noted that the detailed description of the present invention is intended to illustrate only certain embodiments of the claimed invention and are not intended as a means for defining the limits and scope of the invention.

DETAILED DESCRIPTION OF THE PREFERRED EMBODIMENTS

The present invention provides a method that includes the use of the essential oil from Kunzea ambigua for the treatment, or improvement of, various medical conditions. Specifically it has been found that the oil acts positively against parasitic infestation of humans and animals. The oil also has high kill rates against various viruses and germs. Good results have been achieved via inhalation of the fumes of the oil, as well as via indigestion of specific amounts of the essential oil and by way of application of the essential oil of Kunzea ambigua to infected areas, such as would be involved in the treatment of lesions.

In order that the present invention may be more readily understood, there shall be described applications of the invention which are to serve as examples of its use and effectiveness:

A first patient was suffering substantial weight loss over a relatively short period (from 95 Kg to 88 Kg.) The patient was originally suspected of having a thyroid malfunction, but tests did not show more than a minor irregularity and a second diagnoses was lung cancer (although this was not indicated by X-ray). A second opinion was sought and the medical practitioner did certain tests and weighed the patient and asked him to return for the test results after a short period. During this period, the patient self-medicated and settled on taking two doses a day of seven to eight drops of the Kunzea ambigua oil in 16 ml of water, gargled and then swallowed. The results were dramatic, the patient gained weight at a rate of some 0.5 Kg per day. It is the patient's belief that he was, in fact, infested with parasites and the Kunzea ambigua oil killed the infestation and enabled his digestive system to operate normally. The treatment was discontinued after approximately one week on the assumption that the weight gain indicated that the cause of the loss had been removed. After several years the problem has not reoccurred. It is believed that the oil acted as a highly effective anthelmintic.

A second patient who has cancer of the jaw had great success in assisting lesions caused by the cancer both externally, by using Kunzea ambigua externally, together with a source of limonene, and internally by applying the oil, with approximately 20 drops of the essential oil together with a source of limonene, to the lesions and swallowing the material. There have been great improvements in the lesions both in the mouth and those on the face.

A third patient, a middle-aged man with irritable bowel syndrome, self-medicated with four drops each of *Kunzea ambigua* and fragonia (Agonis fragrans) oils three times a day with food. Within a week, the symptoms of the disease disappeared.

Another patient, a person suffering with hemorrhoids inserted four to five drops of *Kunzea ambigua* into his rectum twice in the first day and then daily after bowel movement and by the fifth day the symptoms were substantially relieved.

A further patient, a 65-year-old man having severe gout in the fingers and wrist received external applications in these areas of the essential oils of *Kunzea ambigua* and obtained good results, however, due to the fact that the passage of oil through the skin in these areas is slow, the beneficial effects of the treatment took a period of time longer than had been anticipated. This patient took 5-6 drops of *Kunzea ambigua* in water or fruit juice each morning and after eleven days the swelling had regressed and the pain was substantially relieved. The patient in this case also took conventional pain killers during the early part of the treatment but after five days discontinued this additional form of therapy.

Examples of internal use of the essential oil of *Kunzea ambigua* include the use of three drops per 10 kg of body weight, one or more times, for the treatment of tick fever, also known as scrub typhus. More particularly, the essential oil of *Kunzea ambigua* was used by the patient for five days, at three drops per 10 kg of body weight, every six hours. Results on some patients have found significant improvement in as little as two days of treatment.

Another example of an internal use of the essential oil of *Kunzea ambigua* of the present invention concerned the treatment of a tooth abbess. For treatment of this ailment, the patient again used three drops per 10 kg of body weight every six hours and held the essential oil of *Kunzea ambigua* via an applicator on the infected area of the patient's mouth, preferably, for at least several minutes.

Separately, another patient had a chronic sinus infection. Treatment via steam inhalation of the essential oil of *Kunzea ambigua* proved to be an effective treatment for alleviating the chronic sinus condition of the patient.

The oil has been laboratory tested against viruses and has shown a very high kill rate. It is believed that the oil is efficacious against many diseases caused by internal bacteria and viruses. Several practitioners have reported that they have had patients with cold symptoms and they have found that if these patients inhale *Kunzea ambigua* oil during the early stages of the onset of a common cold, the resulting cold has been much less severe than would have otherwise expected and may not develop into a substantial cold.

The oil can also be used as a general tonic. A few drops a day in water or fruit juice and lead to feeling of well being and can act as a stress relieving agent.

The essential oil of the present invention can also be used to minimize jet lag.

The oil can also be successfully used against parasite attacks in animals.

In Europe, and specifically in France, essential oils are used by mainstream doctors, are prescribed by them for treating certain diseases; the prescriptions are made by pharmacists, are used internally in many applications and are used at higher rates than have generally been the case in Britain, Australia and the United States of America.

Trials of the use of *Kunzea ambigua* oil have been carried out in France by Dr. Daniel Penoel, a leading practitioner in the relevant technical field. These trials have been clinically based and have been done without external funding. Dr. Penoel has stated that using *Kunzea ambigua* in a diluted form and in external applications can only reveal some possibilities. Obviously using higher concentrations and using internally opens up completely new areas of application. What was done with *Kunzea ambigua* in this medical context has confirmed its effectiveness.

As a result of trials conducted, it was found that *Kunzea ambigua* taken internally has shown a very strong effectiveness on a number of viral conditions. In particular internal administration (whether by ingestion or inhalation) has been found to have therapeutic results as follows:

1. *Kunzea ambigua* has shown a strong effect on the cleansing of arteries that were partially clogged by atheromatosis plaques;
2. *Kunzea ambigua* has shown powerful usefulness on degenerative conditions involving certain forms of cancers (veterinary medicine);
3. *Kunzea ambigua* has shown a very significant effectiveness on inflammatory processes, including inflammation linked with auto-immune diseases, and the relief of gout pain;
4. *Kunzea ambigua* has shown a very positive effectiveness for some receptive patients, on the psyche, to give strength and resilience;
5. *Kunzea ambigua* has shown a very strong effectiveness on consequences of chronic and persistent viral infections, like EBV (glandular fever) and cold sores (herpes), with results that no pharmaceutical synthetic molecule has achieved;
6. *Kunzea ambigua* has shown a positive action on the liver function.
7. *Kunzea ambigua* has shown to be an effective treatment of parasitic infestation, i.e. anthelmintic;
8. *Kunzea Ambigua* has been used to treat internal bacterial infections, including MRSA, Delhi Belly, and *Staphylococcus* and/or *Streptococcus* infections; and
9. *Kunzea Ambigua* used in association with other active ingredients, such as limonene and/or fragonia to treat carcinomas (cancerous ulcers) in conjunction with limonene as 10% citrus aurantium to 90% *kunzea ambigua* (include photographic evidence).

Dr. Penoel has also carried out trials on animals and has reported: "In veterinary medicine, it is easy to understand that many treatments can be given that would not be possible in human medicine. Several cases of dogs that should 'normally' have died are still living and *Kunzea ambigua* played a major role in rescuing them. Other animals have been treated with excellent results that were found amazing by the veterinary surgeons. If one understands that *Kunzea ambigua* has a multiple facet action on several aspects of physiopathological processes that underlie many diseases, it is clear that the list of diseases in which it may exert a positive role is extremely vast."

The methods of the present invention may also be used in combination with other active agents, such as, e.g., limonene and/or fragonia. For the treatment of carcinomas (cancerous ulcers), a preferred manner of treatment would be the administration of a preparation comprising limonene at 10% Citrus aurantium to 90% *Kunzea ambigua*.

While only several embodiments of the present invention have been shown and described, it will be obvious to those skilled in the art that many modifications may be made to the present invention without departing from the spirit and scope thereof.

What is claimed is:

1. A method for treating an infectious condition that adversely affects digestion in a human or other animal in need thereof, the method comprising the step of internally administering to said human or other animal an effective amount of a composition comprising an essential oil of *Kunzea ambigua*, as an active ingredient therein.

2. The method according to claim 1, wherein the step of internally administering comprises internally administering 2-15 drops, 2-4 times daily, of the essential oil of *Kunzea ambigua*.

3. The method according to claim 1, wherein the step of internally administering is carried out by internally administering one to three drops of the essential oil of *Kunzea ambigua* per 10 to 15 kilograms of body weight of a human or other animal and repeating said step of internally administering the essential oil of *Kunzea ambigua* every six to 12 hours for 4 to 7 days.

4. The method according to claim 1, wherein the step of internally administering is carried out by internally administering one to three drops of the essential oil per 10 kilograms of body weight of a human or other animal and repeating said step of internally administering the essential oil *Kunzea ambigua* every six hours for at least two days.

5. The method according to claim 1, wherein the composition comprises 90% of the essential oil of *Kunzea ambigua* and 10% Citrus aurantium.

6. The method according to claim 1, wherein the condition is irritable bowel syndrome and composition further comprises fragonia.

7. The method according to claim 1, wherein said step of internally administering is carried out by internally administering three drops of the essential oil of *Kunzea ambigua* per 10 kilograms of body weight of a human or other animal and repeating said step of internally administering the essential oil of *Kunzea ambigua* every six hours.

8. The method according to claim 1, wherein the step of internally administering is carried out by internally administering three drops of the essential oil of *Kunzea ambigua* per 10 kilograms of body weight of a human or other animal and repeating said step of internally administering the essential oil of *Kunzea ambigua* every six hours for at least two days.

\* \* \* \* \*